(12) United States Patent
Cude et al.

(10) Patent No.: US 9,579,497 B2
(45) Date of Patent: Feb. 28, 2017

(54) LUER LOCK ADAPTER

(71) Applicant: Coeur, Inc., Lebanon, TN (US)

(72) Inventors: J. Michael Cude, College Grove, TN (US); Raymond Jozwik, Hendersonville, TN (US)

(73) Assignee: COEUR, INC., Lebanon, TN (US)

( * ) Notice: Subject to any disclaimer, the term of this patent is extended or adjusted under 35 U.S.C. 154(b) by 803 days.

(21) Appl. No.: 13/764,343

(22) Filed: Feb. 11, 2013

(65) Prior Publication Data

US 2013/0158520 A1 Jun. 20, 2013

Related U.S. Application Data

(63) Continuation of application No. 12/249,199, filed on Oct. 10, 2008, now Pat. No. 8,372,057.

(51) Int. Cl.
*A61M 25/16* (2006.01)
*A61M 25/18* (2006.01)
(Continued)

(52) U.S. Cl.
CPC ............. *A61M 39/10* (2013.01); *A61M 39/12* (2013.01); *A61M 2039/1044* (2013.01);
(Continued)

(58) Field of Classification Search
CPC ................. A61M 39/10; A61M 39/12; A61M 2205/582; A61M 2039/1066;
(Continued)

(56) References Cited

U.S. PATENT DOCUMENTS 2,564,804 A * 8/1951 Everett ................. A61M 5/34
285/38
4,294,250 A 10/1981 Dennehey
(Continued)

FOREIGN PATENT DOCUMENTS

DE 3242238 A1 5/1984
DE 20017013 U1 12/2000
(Continued)

OTHER PUBLICATIONS

European Search Report, Search dated Dec. 21, 2010, Application No. 09012835.6-1257/2174687, The Hague.
(Continued)

*Primary Examiner* — Rebecca E Eisenberg
(74) *Attorney, Agent, or Firm* — Hahn Loeser & Parks LLP

(57) ABSTRACT

An adapter for a medical receptacle having an internally threaded skirt with an outside diameter and an inside diameter, and a post within the skirt, includes a proximal end portion having a threaded surface including at least one thread configured to threadingly engage a threaded interior of a skirt of a medical receptacle, and a distal end portion having a surface portion and a generally cylindrical recess. The proximal end portion includes a tapered recess defined by a wall, a chamfer, and a seat and the surface portion includes a gripping mechanism. A conduit is positioned between the tapered recess and the generally cylindrical recess such that the conduit is in fluid communication with both the recess and the generally cylindrical recess.

16 Claims, 5 Drawing Sheets

(51) Int. Cl.
*A61M 39/00* (2006.01)
*A61M 39/10* (2006.01)
*A61M 39/12* (2006.01)

(52) U.S. Cl.
CPC ............... *A61M 2039/1066* (2013.01); *A61M 2039/1077* (2013.01); *A61M 2205/582* (2013.01)

(58) Field of Classification Search
CPC .. A61M 2039/1044; A61M 2039/1077; A61M 39/20; A61M 2039/1016; A61M 2039/1083; A61M 2039/1088; A61M 2039/1027; A61M 5/34; A61M 5/347
USPC .................................................. 604/533–535
See application file for complete search history.

(56) References Cited

U.S. PATENT DOCUMENTS

| | | | |
|---|---|---|---|
| 5,312,377 A | 5/1994 | Dalton | |
| 5,591,143 A | 1/1997 | Trombley et al. | |
| 5,620,427 A * | 4/1997 | Werschmidt | A61M 39/10 137/516.13 |
| 5,651,776 A * | 7/1997 | Appling | A61M 39/10 285/332 |
| 5,782,505 A * | 7/1998 | Brooks | A61M 39/12 285/148.19 |
| 6,332,633 B1 * | 12/2001 | Fitoussi | A61M 39/10 285/332 |
| 6,802,836 B2 | 10/2004 | Bouphavichith et al. | |
| 7,455,325 B2 * | 11/2008 | Mejlhede et al. | 285/286.1 |
| 2004/0155457 A1 | 8/2004 | Mejlhede et al. | |
| 2004/0243065 A1 | 12/2004 | McConnell et al. | |
| 2005/0146136 A1 * | 7/2005 | Kawamura | A61M 39/10 285/255 |
| 2009/0243281 A1 * | 10/2009 | Seifert | A61M 39/1011 285/38 |

FOREIGN PATENT DOCUMENTS

| | | |
|---|---|---|
| EP | 0827760 A2 | 3/1998 |
| GB | 632317 | 11/1949 |
| WO | 2007100396 A2 | 9/2007 |

OTHER PUBLICATIONS

The American Heritage College Dictionary, p. 239, Fourth Edition, Copyright 2002 Houghton Mifflin Company, Boston, Massachusetts, US.

* cited by examiner

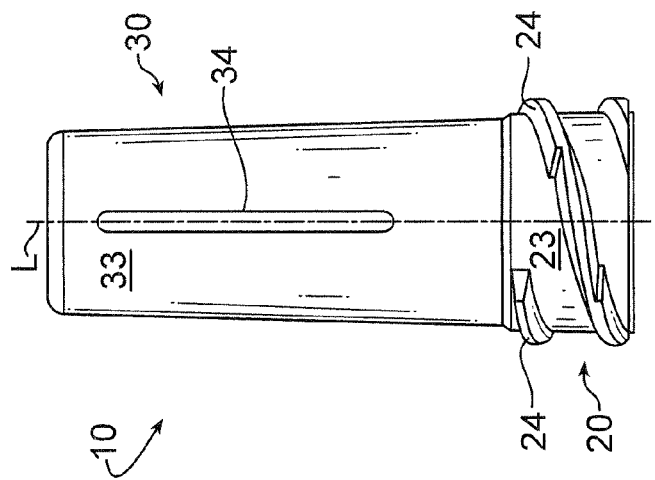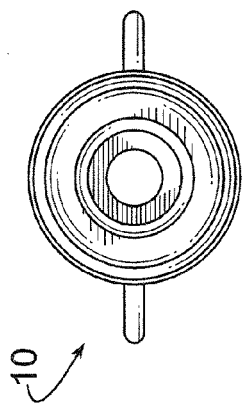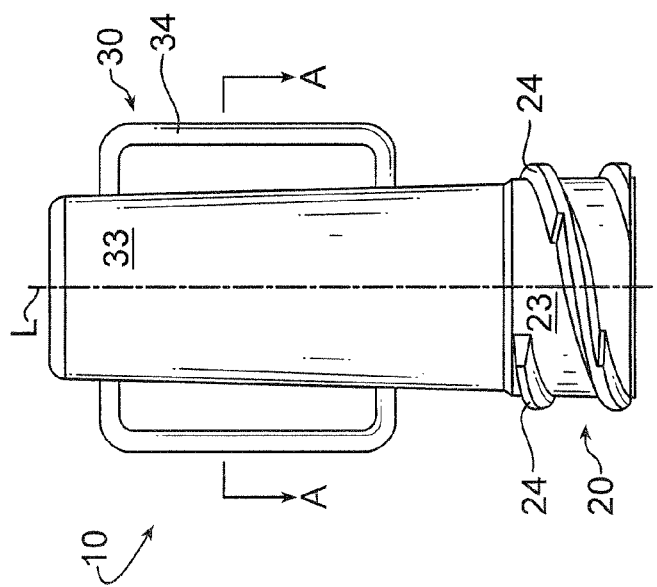

LUER LOCK ADAPTER

CROSS-REFERENCE TO RELATED APPLICATIONS

This application is a continuation of U.S. application Ser. No. 12/249,199, filed Oct. 10, 2008, and claims priority thereto. The disclosure of which application is incorporated herein by reference.

BACKGROUND

This generally pertains to medical equipment, and more particularly to an adapter for medical receptacles, and to a method of attaching an adapter to a medical receptacle.

One well-known receptacle used to connect and establish fluid communication between different medical components is known as a luer lock. Luer receptacles are widely used to connect syringes to medical instruments, such as needles, and to connect medical conduits to one another. In addition, luer lock receptacles have a standard configuration that allows different sizes and types of instruments to be connected to the same receptacle.

A conventional luer connection assembly typically includes a male luer tip component or fitting having a frustoconical shape which is inserted into a female luer component or fitting having a frustoconical shaped receiving cavity. Opposing conical surfaces come into contact with each other to form a sealed friction fit.

There are two general types of luer connection assemblies. One type is generally referred to as the luer slip, where the connection is maintained by the friction fit between the male luer tip and female luer component. The other type is generally referred to as a luer lock connection, whereby the male luer tip is encircled by an annular locking skirt having a threaded internal surface. The female component includes a corresponding single thread formed about the outer surface. Engaging the threaded skirt to the threaded outside surface establishes the connection between the male luer tip and female component while preventing accidental disconnects.

SUMMARY

In one embodiment, an adapter for a medical receptacle having an internally threaded skirt with an outside diameter and an inside diameter, and a post within the skirt, includes a proximal end portion having a threaded surface including at least one thread configured to threadingly engage an internally threaded skirt of a medical receptacle; a distal end portion having a surface portion and a generally cylindrical recess; a conduit positioned between the tapered recess and the generally cylindrical recess such that the conduit is in fluid communication with both the tapered recess and the generally cylindrical recess. The proximal end portion includes a tapered recess defined by a wall, a chamfer, and a seat and the surface portion may include a gripping mechanism.

In at least one embodiment the seat may be perpendicular to a longitudinal axis.

In at least one embodiment the angle formed between the seat and the wall may be approximately 90°.

In at least one other embodiment the angle formed between the seat and the wall may be less than 90°.

In at least one further embodiment the angle formed between the seat and the chamfer may be greater than approximately 90° and less than approximately 180°.

In at least one embodiment the at least one thread may be a plurality of threads.

In at least one further embodiment the plurality of threads may be two threads.

In at least one embodiments the gripping mechanism may be at least two wings extending from the surface portion.

In at least one further embodiment the at least two wings may be substantially parallel to a longitudinal axis.

In at least one other embodiment the at least two wings may be axially at least 5° from a longitudinal axis.

In at least one other embodiment the gripping mechanism may be a plurality of ribs.

In at least one other embodiment the gripping mechanism may be a plurality of knurls.

In at least one further embodiment the surface portion may further includes a collar projecting therefrom.

A methods for securing such adapters to a medical receptacle are also contemplated.

BRIEF DESCRIPTION OF THE DRAWINGS

FIG. 1A is side view of a luer lock adapter;

FIG. 1B is a side view of the luer lock adapter of FIG. 1A rotated 90°;

FIG. 1C is a top view of the luer lock adapter of FIG. 1A;

DETAILED DESCRIPTION

Figure 2:
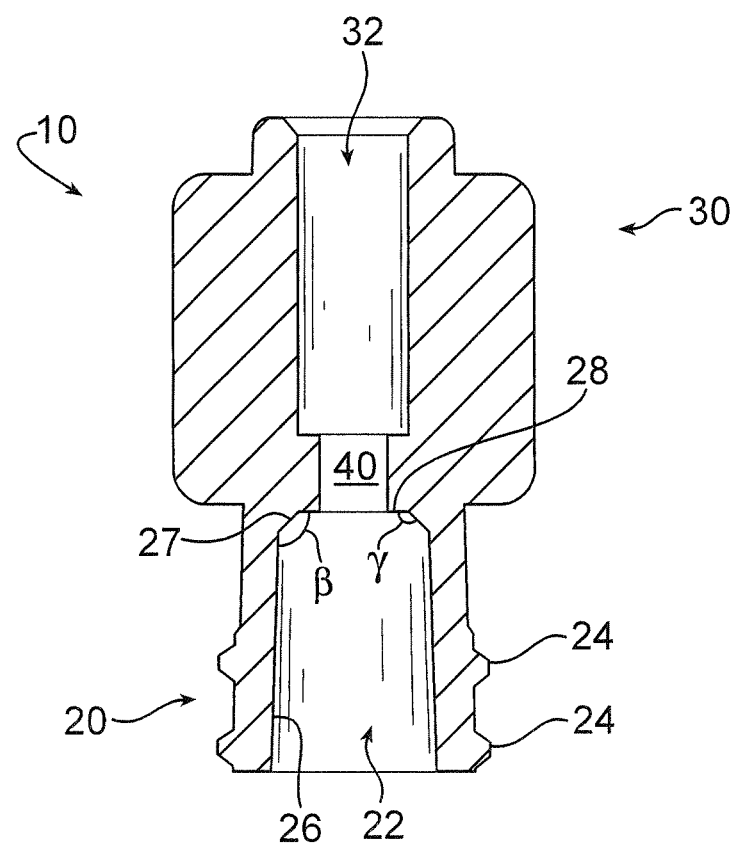
FIG. 2 is a cross-sectional view of the luer lock adapter of FIG. 1A.

Referring now to FIGS. 1A, 1B, 1C and 2, an adapter 10 for attachment to a medical device is illustrated. The adapter 10 may include a proximal end 20 having a tapered recess 22 formed therein. The adapter 10 may also include a distal end 30 having a generally cylindrical recess 32 formed therein. The adapter 10 may also include a conduit 40 formed between the tapered recess 22 and the generally cylindrical recess 32. The conduit 40 may be in fluid communication with both the tapered recess 22 and the generally cylindrical recess 32.

In construction, the adapter 10 may comprise a rigid or semi-rigid material such as metal, hard plastic or a composite. The adapter 10 may be molded, machined or otherwise formed with the required features and dimensions.

Figure 3C:
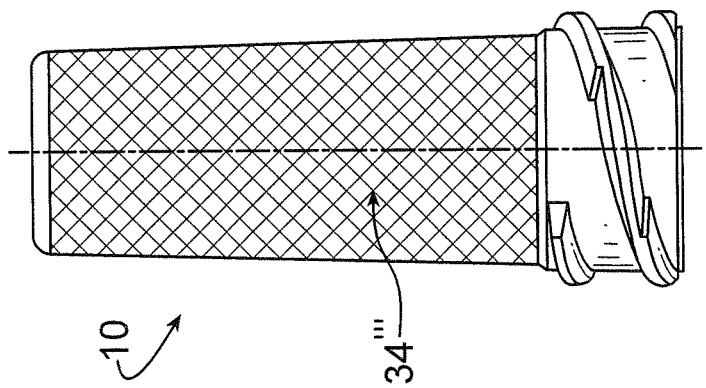
FIG. 3C is a side view of another alternate embodiment of a luer lock adapter.
Figure 3B:
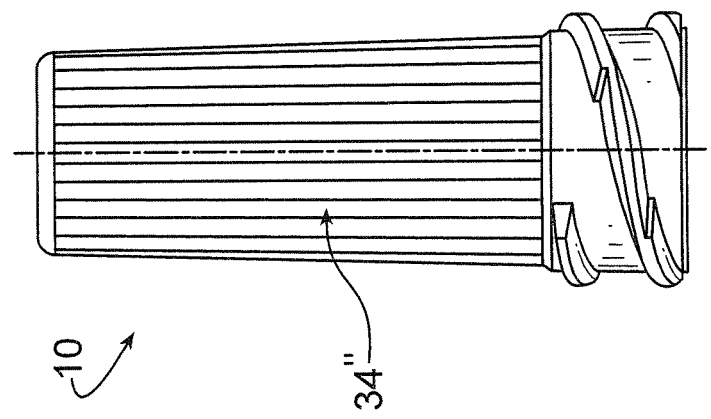
FIG. 3B is a side view of another alternate embodiment of a luer lock adapter.
Figure 3A:
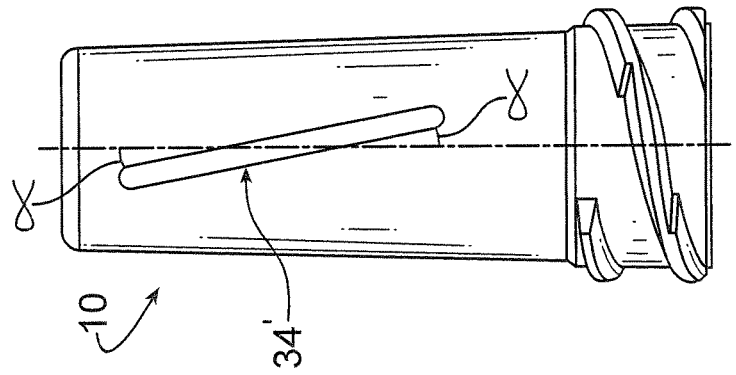
FIG. 3A is a side view of another embodiment of a luer lock adapter.

As shown in FIGS. 1A and 1B, the adapter 10 may be generally cylindrical in shape and may have a longitudinal axis L. The adapter may also include a surface portion 33 which includes a gripping mechanism 34. In one embodiment, the gripping mechanism 34 may comprise at least two wings which extend outwardly from the surface portion 33. It is envisioned that the gripping mechanism 34 are dimensioned such that they may not permit an individual twisting the adapter 10 to achieve sufficient mechanical advantage to over-torque the adapter 10, thereby damaging the adapter and/or the medical device to which the adapter 10 may be attached. The receptacle may be susceptible to damage, for example, at the intersection of the skirt with the syringe barrel as well as at the intersection of the tapered post with the syringe barrel. In an alternate embodiment as shown in FIG. 3A, the gripping mechanism 34' may include at least two wings which may be spaced approximately 180° apart about the surface portion 33 and are angled axially by an angle α. The angle α may be chosen such that when a user attempts to over-torque the adapter 10, the user's fingers may slip off of the gripping mechanism, thereby preventing over-torqueing. For example, angle α may be 5°. In other alternate embodiments, the gripping mechanism may be ribs 34", as shown in FIG. 3B, or knurls 34''', as shown in FIG. 3C.

As shown in FIG. 2, the adapter 10 may include a tapered recess 22 defined by an interior wall 26, a chamfer 27, and a seat 28. In one embodiment, the seat 28 may be perpendicular to the longitudinal axis L. It is also envisioned that the angle between the seat 28 and the wall 26, angle β, may be approximately 90°. Furthermore, it is envisioned that the angle β may be less than 90° in instances where the seat 28 is angled toward and into the tapered recess 22, rather than being oriented approximately perpendicular to the longitudinal axis L. It is also envisioned that the angle between the seat 28 and the chamfer 27, angle γ, may be between approximately 90° and approximately 180°.

Figure 4:
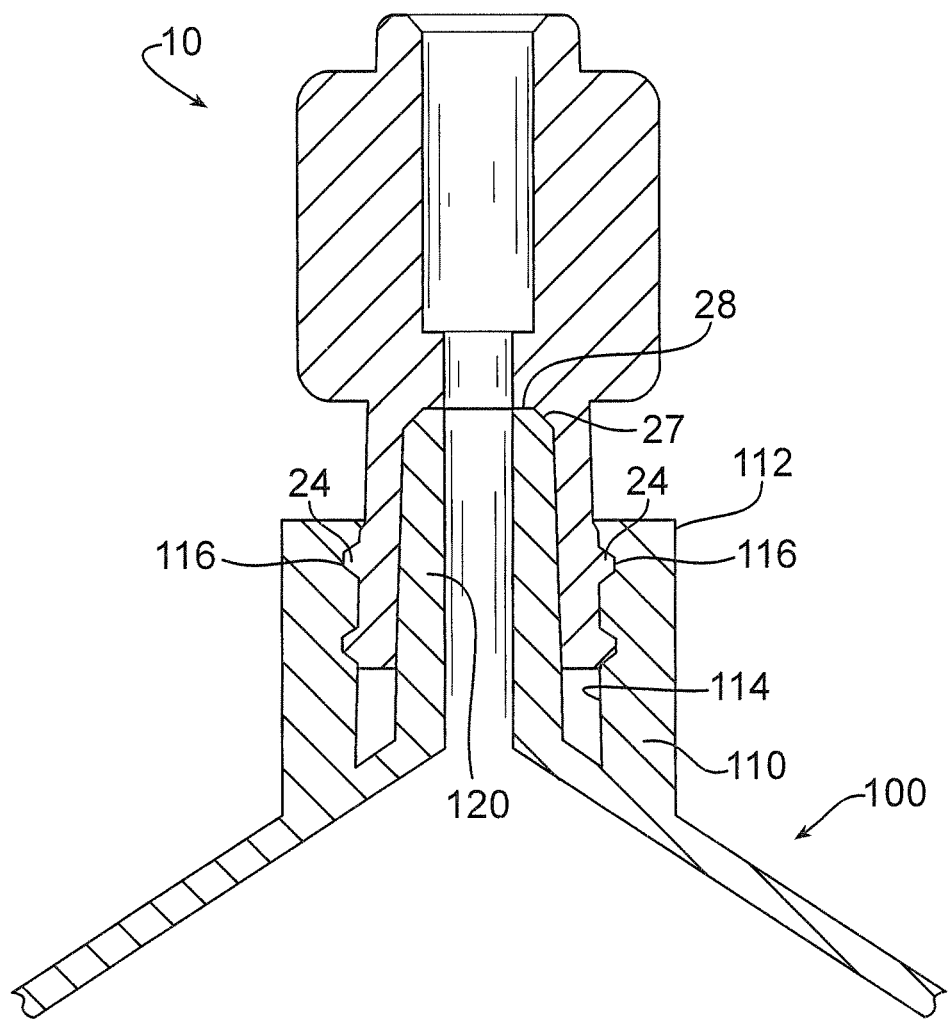
FIG. 4 is a cross-sectional view of the luer lock adapter of FIG. 1A attached to a medical receptacle.

Referring now to FIG. 4, the distal end of the adapter 30 may also include a generally cylindrical recess 32, into which a medical instrument, including medical tubing or needles, may be affixed by a suitable method such as such as welding, brazing or press fitting. Alternately, the adapter 10 and the medical instrument may be machined or molded from a same piece of material.

Referring again to FIG. 1A, The adapter 10 may also include a proximal end 20 having a threaded surface 23. The threaded surface 23 may include at least one thread 24 extending therefrom. The at least one thread 24 may facilitate threading engagement with a medical receptacle which may have a skirt with an outside diameter and a threaded inside diameter. In one embodiment, the at least one thread 24 may be a plurality of threads. In another embodiment, the at least one thread 24 may be two threads. Specifically, the thread configuration may be of the double-start, double-thread variety.

With reference again to FIG. 4, the adapter 10 may be threadingly attached to medical receptacle 100 having a skirt 110 with an outside diameter 112 and an inside diameter 114 which may include threads 116. The at least one thread 24 may be configured such that the at least one thread 24 may threadingly engage the threads 116 of the inside diameter of the skirt 110. Providing the at least one thread 24 as two threads may result in increased contact between the at least one thread 24 and the threads 116 of the medical receptacle 116. As indicated by the configuration of the at least one thread 24 in FIG. 4, the at least one thread 24 contacts the skirt threads 116 at two points spaced approximately 180° apart on the diameter of the adapter 10. Thus, if a force perpendicular to the longitudinal axis L is applied to the adapter 10 from one direction, the at least one thread 24 on the side of the adapter 10 from which the force is applied may tend to deflect upward and contact the top surface of the corresponding thread 116. In contrast, the at least one thread 24 on the opposite side of the adapter 10 from which the force is applied may tend to deflect downward and contact the bottom surface of the corresponding thread 116, thereby creating two points of contact between the adapter 10 and the receptacle 100 and providing additional resistance to the applied force. In contrast, prior art adapters may include only one thread and thus have only one point of contact with the receptacle. As there is no second point of contact between the receptacle and the adapters of the prior art, the force applied to a prior art adapter may likely crack the threads attached to the adapter or in extreme cases, shear the threads from the adapter completely. Thus, it is envisioned that the at least one thread 24 is designed to achieve sufficient mechanical advantage such that this type of damage to the adapter 10, as well damage at the intersection of the skirt 110 with the syringe barrel and at the intersection of the tapered post 120 with the syringe barrel, is thereby reduced when the adapter 10 is subjected to forces perpendicular to its longitudinal axis L.

With continued reference to FIG. 4, the adapter 10 may be attached to the receptacle 100 by aligning the tapered post 120 of the receptacle 110 with the tapered recess 22 and pressing the adapter 10 onto the tapered post 120 while simultaneously engaging the at least one thread 24 with the threads 116 of the skirt 110. While twisting the adapter 10, the end of the tapered post 120 may contact the seat 28, at which point the user may feel resistance, which may indicate that the adapter 10 has been fully engaged with the receptacle 100. By contrast, prior art tapered recesses have not included seats such as those presently disclosed, whereby over-torqueing and resultant damage to tapered posts are therefore common occurrences.

Figure 5:
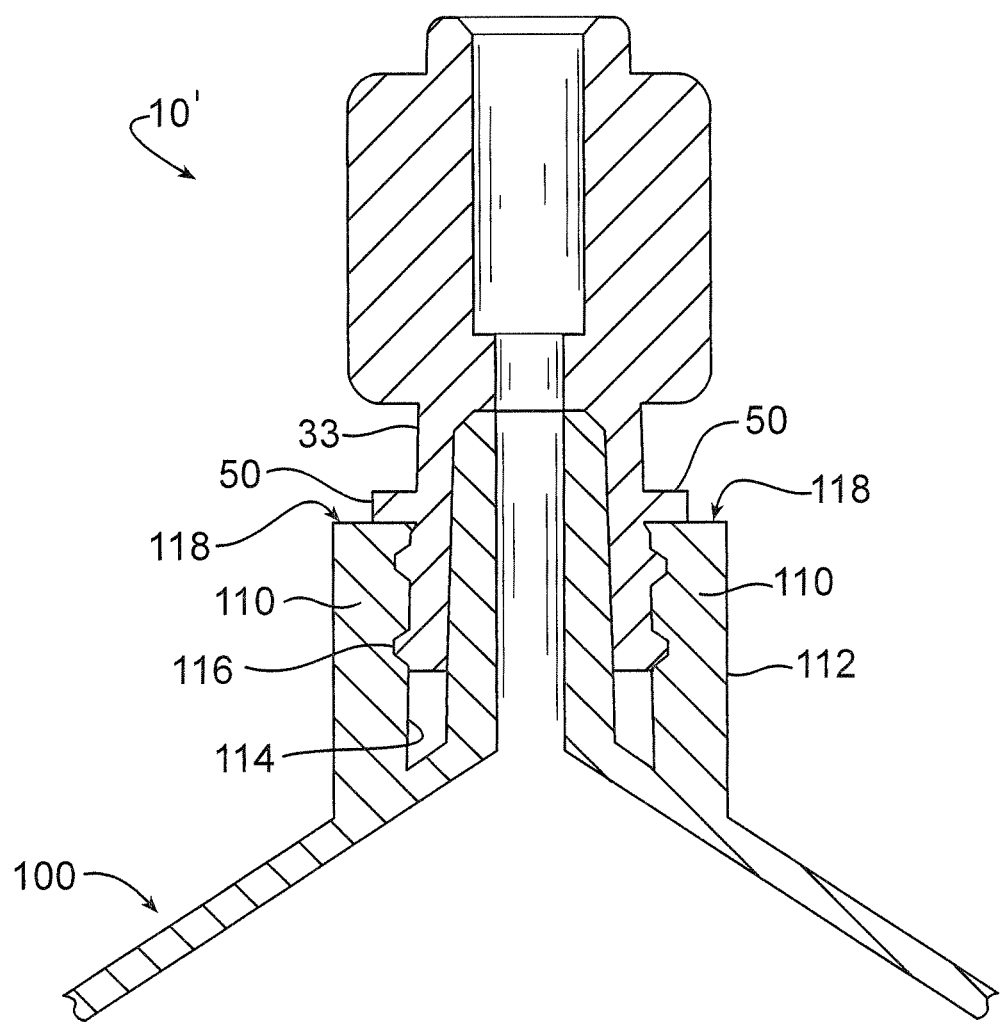
FIG. 5 is a cross-sectional view of an alternate embodiment of a luer lock adapter attached to a medical receptacle.

In an alternate embodiment shown in FIG. 5, the adapter 10' may include a collar 50 which extends from the surface portion 32. Thus, as the adapter 10' is attached to the receptacle 100, the collar 50 may contact a top surface 118 of the skirt 100, such that the collar 50 acts as a mechanical stop which may prevent a user from over-torqueing the adapter 10', thus preventing damage to the adapter 10' and the medical receptacle 100. Furthermore, the collar 50 may also act as a visual cue to the user attaching the adapter 10' to the receptacle 100, in that a gap between the collar 50 and the top surface 118 may be present until the adapter 10' has been sufficiently tightened. Thus, a user may be signaled that the adapter 10' has been sufficiently tightened once any gap has disappeared.

While principles and modes of operation have been explained and illustrated with regard to particular embodiments, it must be understood, however, that this may be practiced otherwise than as specifically explained and illustrated without departing from its spirit or scope.

What is claimed is:

1. An adapter for a medical receptacle having an internally threaded skirt with an outside diameter and an inside diameter, and a post within the skirt, the adapter comprising:
   a proximal end portion having a threaded surface including at least one thread configured to threadingly engage a threaded interior of a skirt of a medical receptacle, the proximal end portion including a tapered recess defined by a wall, and a chamfer having a transition from the wall to a seat, the seat having a diameter,
   a distal end portion having a surface portion including a collar, a gripping mechanism and a generally cylindrical recess having a diameter, wherein the collar projects from the surface portion to act as a mechanical stop, and wherein the gripping mechanism is at least two planar wings extending from the surface portion, all portions of the at least two planar wings being angled axially at least 5° from a longitudinal axis; and
   a conduit positioned between the tapered recess and the generally cylindrical recess such that the conduit is in fluid communication with both the tapered recess and the generally cylindrical recess, the generally cylindrical recess and the tapered recess spaced apart by the length of the conduit, the length of the conduit having a diameter smaller than both the seat diameter and the generally cylindrical recess diameter.

2. The adapter of claim 1, wherein the seat is perpendicular to a longitudinal axis.

3. The adapter of claim 1, wherein an angle formed between the seat and the wall is approximately 90°.

4. The adapter of claim 1, wherein an angle formed between the seat and the wall is less than 90°.

5. The adapter of claim 1, wherein an angle formed between the seat and the chamfer is greater than approximately 90° and less than approximately 180°.

6. The adapter of claim 1, wherein the at least one thread is a plurality of threads.

7. The adapter of claim 6, wherein the plurality of threads is two threads.

8. The adapter of claim 1, wherein the gripping mechanism further comprises a plurality of ribs.

9. The adapter of claim 1, wherein the gripping mechanism further comprises a plurality of knurls.

10. A method for securing an adapter to a medical receptacle having an internally threaded skirt with an outside diameter and an inside diameter, and a post within the skirt comprising the steps of:
   (a) providing an adapter including:
      a proximal end portion having a threaded surface including at least one thread configured to threadingly engage a threaded interior of a skirt of a medical receptacle, the proximal end portion including a tapered recess defined by a wall, and a chamfer having a transition from the wall to a seat, seat having a diameter;
      a distal end portion having a surface portion including a collar, a gripping mechanism and a generally cylindrical recess having a diameter, wherein the collar projects from the surface portion to act as a mechanical stop, and wherein the gripping mechanism is at least two planar wings extending from the surface portion, all portions of the at least two planar wings being angled axially at least 5° from a longitudinal axis; and
      a conduit positioned between the tapered recess and the generally cylindrical recess such that the conduit is in fluid communication with both the tapered recess and the generally cylindrical recess and the generally cylindrical recess and the tapered recess are spaced apart by the length of the conduit, the conduit having a diameter smaller than both the seat diameter and the generally cylindrical recess diameter;
   (b) inserting a post of a medical receptacle into the tapered recess; and
   (c) twisting the adapter to engage the at least one thread of the adapter with an internally threaded skirt the medical receptacle.

11. The method of claim 10, wherein the seat is perpendicular to a longitudinal axis of the adapter.

12. The method of claim 10, wherein the at least one thread is a plurality of threads.

13. The method of claim 12, wherein the plurality of threads is two threads.

14. A method for securing an adapter to a medical receptacle having an internally threaded skirt with an outside diameter, an inside diameter and an upper surface, and a post within the skirt, comprising the steps of:
   (a) providing an adapter including: a proximal end portion having a threaded surface including at least one thread configured to threadingly engage a threaded interior of a skirt of a medical receptacle, the proximal end portion including a tapered recess defined by a wall, and a chamfer having a transition from the wall to a seat, the seat having a diameter, the proximal end portion including a collar projecting from the threaded surface
      a distal end portion having a surface portion including a collar, a gripping mechanism and a generally cylindrical recess having a diameter, wherein the collar projects from the surface portion to act as a mechanical stop, and wherein the gripping mechanism is at least two planar wings extending from the surface portion, all portions of the at least two planar wings being angled axially at least 5° from a longitudinal axis, and
      a conduit positioned between the tapered recess and the generally cylindrical recess such that the conduit is in fluid communication with both the tapered recess and the generally cylindrical recess and the generally cylindrical recess and the tapered recess are spaced apart by the length of the conduit, the conduit having a diameter smaller than both the seat diameter and the generally cylindrical recess diameter;
   (b) inserting a post of a medical receptacle into the tapered recess; and
   (c) twisting the adapter to engage the at least one thread of the adapter with a threaded interior of a skirt of the medical receptacle until the collar contacts an upper surface of the skirt.

15. The adapter of claim 1, wherein the at least two planar wings are angled axially approximately 5° from the longitudinal axis.

16. The adapter of claim 1, wherein the at least two planar wings are angled axially at 5° from the longitudinal axis.

* * * * *